United States Patent

Roydhouse

[11] Patent Number: 5,093,024
[45] Date of Patent: Mar. 3, 1992

[54] COMPOSITION ABLE TO ABSORB MERCURY VAPOR AND TO DISINFECT A SURFACE

[75] Inventor: Richard H. Roydhouse, Vancouver, Canada

[73] Assignee: EPS Environmental Protection Systems Limited, Canada

[21] Appl. No.: 449,126

[22] Filed: Dec. 8, 1989

Related U.S. Application Data

[63] Continuation of Ser. No. 241,750, Sep. 8, 1988, abandoned, which is a continuation-in-part of Ser. No. 118,596, Nov. 11, 1987, abandoned.

[51] Int. Cl.$^5$ ................................................ C11D 3/48
[52] U.S. Cl. ............................ 252/186.34; 252/184; 252/106; 422/37
[58] Field of Search ................. 252/106, 184, 186.34; 423/210; 210/914; 422/37

[56] References Cited

U.S. PATENT DOCUMENTS

| | | | |
|---|---|---|---|
| 3,647,359 | 3/1972 | Bell | 23/2 R |
| 3,764,496 | 10/1973 | Hultman | 204/99 |
| 4,083,795 | 4/1978 | Joubert | 252/99 |
| 4,249,274 | 2/1981 | Kitko | 4/227 |
| 4,534,944 | 8/1985 | Rodyhouse | 423/210 |
| 4,539,179 | 9/1985 | Meloy | 422/28 |

FOREIGN PATENT DOCUMENTS 0858460 3/1978 Belgium .
0886955 7/1981 U.S.S.R. .

Primary Examiner—Prince Willis, Jr.
Assistant Examiner—J. Silbermann
Attorney, Agent, or Firm—Townsend and Townsend

[57] ABSTRACT

A composition able to absorb mercury vapor and to disinfect a surface. The composition has
a source of halogen; and
a non-aqueous solvent of low vapor pressure for the source of halogen. The composition is of low vapor pressure.

1 Claim, No Drawings

COMPOSITION ABLE TO ABSORB MERCURY VAPOR AND TO DISINFECT A SURFACE

FIELD OF THE INVENTION

This invention relates to methods and compositions able to absorb mercury vapour and disinfect a surface.

DESCRIPTION OF THE PRIOR ART

Dental and other medical (e.g. hospital operating theatres) plumbing such as tubing, piping, traps and suction units are a breeding ground and collection site for a myriad of bacteria and viruses. In dental offices this biological hazard is further complicated by the backflow of mercury vapour from silver amalgam debris. Infections to both patients and staff can occur from micro-organisms within evacuation systems and drains. Large quantities of both organic and microbial matter, and mercury rich material collect in the suction traps. Personnel performing routine cleaning of these traps are at hazard to high concentrations of contaminants. Several water based solutions are available to help clean, disinfect and deodorize evacuation systems. These solutions rely on either quaternary ammonium salts or proteolytic enzymes to kill bacteria and viruses. Both of these agents need to be in contact with the target microbe for several minutes or in some cases hours in order to be effective. They have no demonstrated ability to absorb mercury vapours. Although aqueous disinfectants based on hypochlorite are good disinfectants and mercury absorbers, they have low viscosity and are suctioned through systems rapidly due to their very high water content. Therefore, most of the active ingredient in prior art formulations provide only very short term disinfection and mercury vapour suppression properties.

For instance, Usole in Soviet Patent 886955 describes mercury vapour absorbing compositions containing di- and tri-valent iron and aluminum chloride(s), silica, hydrochloric acid and water. A typical absorbing solution contains in weight per cent 9-23 ferric chloride, 0.4-0.8 ferrous chloride, 5-14 aluminum chloride, 1-3 hydrochloric acid, 0.8-22 silicon dioxide and the balance as water. Such a low viscosity, aqueous composition is highly corrosive to metallic plumbing due to its acidic nature and is unsuitable as a storage medium for bactericides or viricides, especially those based on halogens e.g. chloramine T which can rapidly release gaseous molecular halogens (e.g. chlorine) at highly acidic (e.g. pH 2) conditions. Clearly, such compositions are unsuitable for absorbing mercury vapour and disinfecting surfaces in medical or dental operations.

Roydhouse in U.S. Pat. No. 4,534,944 describes thiosulphate containing formulations for absorbing mercury vapour. Although the formulations are satisfactory for mercury vapour suppression in stationary environments, they are unsuitable for use in dental/medical evacuation systems for the following reasons:

1) the thiosulphate or sulphur or isopropyl alcohol containing formulations will destroy disinfectants based on chlorine due to oxidation/reduction reactions.
2) these low viscosity formulations containing water or isopropyl alcohol are rapidly rinsed from plumbing surfaces in the presence of water or pushed through the plumbing due to the high vacuum of the suction system. In this regard air velocity through the system may be about 6 ft/second.
3) these formulations do not have sufficient disinfectant capability.

The present invention on the other hand describes viscous fluid or solid compositions able to absorb mercury vapour and to disinfect surfaces and having the following unique characteristics:

1) will not evapourate on prolonged standing due to their very low vapour pressure.
2) contain a halogen based disinfectant and mercury vapour suppressant which becomes active on exposure to moisture, whether that moisture is fluid water or moist air.
3) contain alkaline, inorganic pH modifiers which enhance the stability of the halogen containing disinfectant/mercury vapour suppressant and prevent chemical corrosion of the plumbing apparatus.
4) contain inorganic components which allow controllable increase or decrease of the composition viscosity.
5) resist rapid dilution by water.
6) have very good shelf life.

SUMMARY OF THE INVENTION

Accordingly, the present invention provides a composition able to absorb mercury vapour and to disinfect the surface, the composition comprising:
(a) a source of halogen;
(b) a non-aqueous solvent of low vapour pressure for the source of halogen
whereby the composition is of high viscosity and low vapour pressure.

In a preferred embodiment the halogen is chlorine. The source of chlorine may, for example, be chloramine B or dichloro-s-triazinetrione.

The compositions are used in non-aqueous solution, in which the solvent is of low vapour pressure. Polyols, for example, propylene glycol, are preferred.

In a preferred embodiment a thickener may be added and is a compound containing silicon, for example, the silicon compound may be silica.

In this preferred embodiment the silica is present in the range of 0 to 15% by weight of the composition, depending on the thickness required.

pH modifiers may be used to enhance the non-aqueous composition properties. These modifiers include sodium polyphosphates and sodium hexametaphosphate, carbonate, sodium hydroxide and sodium pyrophosphate.

The following formulas illustrate novel mercury vapour suppressant/disinfectant compositions:

FORMULA 1

| Component | % by Weight |
| --- | --- |
| propylene glycol | 83.83 |
| sodium carbonate | 0.10 |
| sodium pyrophosphate | 0.50 |
| Chloramine B | 1.07 |
| Silica* | 14.10 |
| Sodium hydroxide | 0.40 |
| Total: | 100.00 |

*e.g. Zeothix 95 produced by J. Huber Corporation of Etowah, Tennessee.

The sodium containing compounds (pH modifiers) in formula 1 make it alkaline, and act to buffer it against Chloramine B (disinfectant/mercury absorber) decay during storage. The propylene glycol is a low vapour pressure, viscous, non-toxic, chemically inert solvent for the Chloramine B reagent. The silica acts as a chemically inert thickener for the formula, increasing its ability to resist dilution by water (see also experiment 1 below). Chloramine B releases its active chlorine at a slower rate than most other chlorine containing compounds such as hypochlorites. This composition has an initial active chlorine level of 3500 parts per million as measured by titration with sodium thiosulphate in the presence of iodide. It has been found to have a half life of about 368 days when stored in the dark. Even when exposed to sunlight and fluorescent light, this formula has a half life of 101 days.

Table 1 below demonstrates the effect of formula 1 on mercury vapour suppression. Mercury (0.2 g) was added to water diluted and undiluted formula 1 contained in a 50 ml. glass flask. The flask was stoppered and the mercury vapour in the flask was measured at various time intervals using the method described in U.S. Pat. No. 4,534,944, the disclosure of which is incorporated by reference.

TABLE 1

| mL of formula 1 | mL of water | drops of Hcl | pH | Mercury Vapour Concentration in Micrograms/Cubic Meter at Various Times (in hours) | | |
|---|---|---|---|---|---|---|
| | | | | 1 | 2 | 72 |
| 10 | 0 | 0 | 9.81 | 27 | 8 | 0 |
| 5 | 5 | 0 | 9.77 | 375 | 208 | 260 |
| 5 | 5 | 1 | 5.71 | 0 | 0 | 0 |
| 0 | 10 | 0 | — | 4700 | 4600 | 4400 |

FORMULA 2

| Component | % by Weight |
|---|---|
| propylene glycol | 95.45 |
| sodium carbonate | 0.10 |
| sodium hexametaphosphate | 0.20 |
| Chloramine T | 1.20 |
| Silica* | 3.00 |
| Hydrochloric Acid | 0.05 |
| Total: | 100.00 |

*e.g. Aerosil 200 produced by Degussa Corp. of Teterboro, N.J.

Chloramine T is a much less expensive mercury vapour suppressant/disinfectant than Chloramine B. This formula has a pH of 9 immediately after preparation. It has a very good shelf life and mercury vapour suppressing characteristics. It retained 75% of its active chlorine content after 62 days exposure to sunlight and fluorescent light when stored in a white opaque plastic container. Its shelf life is considerably better when stored in the dark.

Table 2 below demonstrates the effect of formula 2 on mercury vapour suppression. Mercury (0.5 g) was added to water diluted and undiluted formula 73B contained in a 50 mL glass flask. The flask was stoppered and the mercury vapour in the flask was measured at various time intervals using the method described in U.S. Pat. No. 4,534,944.

TABLE 2

| mL of formula 2 | mL of water | Mercury Vapour Concentration in Micrograms/Cubic Meter at Various Times (in hours) | | |
|---|---|---|---|---|
| | | 1 | 3 | 24 |
| 1 | 0 | — | 10 | 393 |

TABLE 2-continued

| mL of formula 2 | mL of water | Mercury Vapour Concentration in Micrograms/Cubic Meter at Various Times (in hours) | | |
|---|---|---|---|---|
| | | 1 | 3 | 24 |
| 1 | 9 | 25 | 15 | 15 |
| 0 | 0 | 5517 | 6900 | 5617 |

These results indicate that the mercury suppressing property of this formula remains in the presence or absence of water. Like formula 1 above its mercury suppression properties are enhanced on exposure to moisture.

EXPERIMENT 1

"Coating Pipe"

It has been mentioned that the silica acts as a thickener to produce viscous fluids such as those shown above, with properties unlike the usual aqueous hypochlorite based systems. In a drain or pipe, these and other aqueous solutions drain away rapidly, whereas our formulations persist. This is proved in the following experiment which we carried out:

1. Air was sucked vertically through a clear plastic tube of 1.2 cm diameter at a flowrate of 0.13 cubic meters/minute which is typical of medical/dental suction units.
2. Fifteen milliliter (mL) samples of our various viscous silica containing fluids such as formulas 1 and 72 above were introduced into the bottom of the pipe.

It was found that these viscous fluids rose up the walls of the tubes to levels between 0.57 to 1.3 meters depending mainly on the silica content of the fluid. Lower silica levels gave lower viscosity fluids which travelled longer distances. All aqueous solutions such as those based on hypochlorite (e.g. household bleach) disappeared from the tube almost instantaneously. This is attributed to the extremely high air velocity of medical/dental suctions systems. However, our viscous silica containing fluids produced adherent films on the inside of the pipe of 0.04 to 0.40 millimeter thickness. These films did not dry out due to their extremely low vapour pressure. They remain on the tubing wall to release their active mercury vapour suppressant/disinfectant for prolonged periods whether the suction system is turned on or off.

The prolonged contact with the debris and with organisms on the inner surface of the tube increases the disinfectant and mercury vapour suppressant effect.

FORMULA 3

| Component | % by Weight |
|---|---|
| water | 10.00 |
| sodium carbonate | 0.10 |
| Chloramine B | 2.14 |
| Sodium silicate | 81.76 |
| Silica* | 6.00 |
| Total: | 100.00 |

*e.g. Zeothix 95

Formula 3 is a solid which can be molded into a variety of shapes including spheres, tablets, rods, etc. This material is designed to be placed in the "traps" of dental suction units where it will slowly be dissolved by the liquids in the trap. Such material is designed to remain in the trap for a week or longer. It is designed to work in the location where mercury vapour and microorganisms are expected to be at their highest levels. The main constituent, sodium silicate, acts as a buffer, maintaining the initial tablet pH at 12. The sodium silicate also imparts some water resistance to the tablet and helps solidify the formulation on exposure to air. One tablet (19.5 grams) placed in 1300 mL of water at room temperature took 7 days to dissolve.

Other formulations both in fluid or solid form can be developed having a variety of flow characteristics or shapes respectively. For instance active halogen substitutes such as sodium bichloro-s-traizinetrione and trichloro-s-triazinetrione can be used. Other pH modifiers such as trisodium phosphate and polyphosphates can be used. Various forms of silicates and phosphates may also be used to produce formulas with a wide variety of flow characteristics. Other oxidation resistant glycols could be substituted for propylene glycol. Chemically inert coating such as waxes might be applied to portions of the solid formulations to alter their solubility characteristics in the presence of water or bodily fluids. All of the above-mentioned formulations have the tremendous advantage of not requiring metering apparatus such as those associated with conventional disinfectant formulae. It should be noted that silica free fluid formulae are also possible and that they will have lower viscosities than the silica containing formulae described above.

This is of value, particularly in very long distance pipe where adequate coating of the pipe is difficult to achieve. Such a composition is set out in Formula 4.

FORMULA 4

| Component | % by Weight |
|---|---|
| propylene glycol | 98.40 |
| sodium carbonate | 0.10 |
| sodium hexametaphosphate | 0.21 |
| Chloramine T | 1.24 |
| Hydrochloric Acid | 0.05 |
| Total: | 100.00 |

I claim:
1. A composition able to absorb mercury vapour and to disinfect a surface, the composition comprising:
   (a) about 1.07% to about 2.14% by weight of a halogen source selected from the group consisting of chloramine B and dichloro-s-triazinetrione; and
   (b) about 83.83% to about 95.45% by weight of a polyol of low vapour pressure as a solvent for said halogen source;
whereby the composition is of low vapour pressure, the balance of the composition being compound to thickened the composition and an alkaline compound to stabilize said halogen source.

* * * * *